(12) United States Patent
Kawada et al.

(10) Patent No.: US 7,511,272 B2
(45) Date of Patent: Mar. 31, 2009

(54) METHOD FOR CONTROLLING CHARGED PARTICLE BEAM, AND CHARGED PARTICLE BEAM APPARATUS

(75) Inventors: Hiroki Kawada, Tsuchiura (JP); Ryo Nakagaki, Kawasaki (JP)

(73) Assignee: Hitachi High-Technologies Corporation, Tokyo (JP)

(*) Notice: Subject to any disclaimer, the term of this patent is extended or adjusted under 35 U.S.C. 154(b) by 294 days.

(21) Appl. No.: 11/607,928

(22) Filed: Dec. 4, 2006

(65) Prior Publication Data

US 2007/0085020 A1    Apr. 19, 2007

Related U.S. Application Data

(63) Continuation of application No. 11/127,248, filed on May 12, 2005, now Pat. No. 7,154,090.

(30) Foreign Application Priority Data

May 14, 2004    (JP) .............................. 2004-144284

(51) Int. Cl.
  G01N 23/00    (2006.01)
  G21K 7/00    (2006.01)
  A61N 5/00    (2006.01)
(52) U.S. Cl. .................. 250/310; 250/306; 250/307
(58) Field of Classification Search ................. None
  See application file for complete search history.

(56) References Cited

U.S. PATENT DOCUMENTS

| | | | |
|---|---|---|---|
| 5,387,793 A * | 2/1995 | Sato et al. .................... 250/310 |
| 6,147,355 A | 11/2000 | Ando et al. |
| 6,437,330 B1 | 8/2002 | Sugiyama |
| 6,768,114 B2 | 7/2004 | Takagi |
| 6,838,667 B2 | 1/2005 | Tsuneta et al. |
| 6,864,493 B2 * | 3/2005 | Sato et al. ................. 250/491.1 |
| 7,078,691 B2 * | 7/2006 | Nakayama ................... 250/311 |
| 7,154,090 B2 * | 12/2006 | Kawada et al. .............. 250/310 |

(Continued)

FOREIGN PATENT DOCUMENTS

JP    62-169458    10/1987

(Continued)

OTHER PUBLICATIONS

Japanese Office Action, with English Translation, issued in Japanese Patent Application No. 2004-144284, dated on Oct. 2, 2007.

(Continued)

*Primary Examiner*—David A. Vanore
(74) *Attorney, Agent, or Firm*—McDermott Will & Emery LLP (57) ABSTRACT

According to the invention, to achieve the above objective, there is provided a charged particle beam apparatus that creates a first image by irradiating a charged particle beam on a sample to scan a first pattern of the sample, controls on the basis of the first image the focus of the charged particle beam and the brightness and/or contrast of the image, and irradiates the charged particle beam to correctly scan a second pattern different from the first pattern by using the control conditions used to control the focus of the charged particle beam and the brightness and/or contrast of the image.

9 Claims, 4 Drawing Sheets

U.S. PATENT DOCUMENTS

| | | | |
|---|---|---|---|
| 7,361,894 B2 * | 4/2008 | Sato et al. | 250/306 |
| 7,361,895 B2 * | 4/2008 | Nakasuji et al. | 250/310 |
| 7,361,898 B2 * | 4/2008 | Mizuno et al. | 250/331 |
| 7,446,313 B2 * | 11/2008 | Maeda | 250/310 |
| 2003/0106999 A1 | 6/2003 | Komuro et al. | |
| 2004/0051040 A1 | 3/2004 | Nasu et al. | |

FOREIGN PATENT DOCUMENTS

| | | |
|---|---|---|
| JP | 63-254649 | 10/1988 |
| JP | 04-2699613 | 9/1992 |
| JP | 09-134948 | 5/1997 |
| JP | 10-027839 | 1/1998 |
| JP | 2001-068048 A | 3/2001 |
| JP | 2001-148230 | 5/2001 |
| JP | 2002-245960 | 8/2002 |
| JP | 2003-149302 | 5/2003 |
| JP | 2003-303566 | 10/2003 |
| WO | WO 03/021186 | 3/2003 |

OTHER PUBLICATIONS

Japanese Office Action, with Partial English Translation, issued in Japanese Patent Application No. JP 2007-317834 dated on Aug. 26, 2008.

* cited by examiner

EFFECT OF SHRINKAGE REDUCTION

503 MEASURED VALUE OBTAINED BY METHOD ACCORDING TO THE INVENTION

504 SHRINKAGE CAUSED BY METHOD ACCORDING TO THE INVENTION

501 MEASURED VALUE WITH ELECTRON BEAM IRRADIATED FOR AFC AND ABCC

502 SHRINKAGE WITH ELECTRON BEAM IRRADIATED FOR AFC AND ABCC

FIG.5

METHOD FOR CONTROLLING CHARGED PARTICLE BEAM, AND CHARGED PARTICLE BEAM APPARATUS

RELATED APPLICATIONS

This application is a continuation of application Ser. No. 11/127,248, filed on May 12, 2005 now U.S. Pat. No. 7,154,090, which in turn claims the benefit of Japanese Patent Application No. 2004-1442844 filed on May 14, 2004, the disclosures of which Applications are incorporated by reference herein.

BACKGROUND OF THE INVENTION

The present invention generally relates to a method for controlling a charged particle beam and to a charged particle beam apparatus, and particularly to a method and apparatus for controlling the focus, brightness and/or contrast of the charged particle beam.

In the production/inspection processes for products of function elements such as semiconductor devices and thin-film magnetic heads produced by surface micro fabrication, a scanning electron microscope (hereinafter, referred to as SEM) is widely used to measure the line widths of the formed patterns (hereinafter, simply said as "measure", "measurement", "measured" and so on) and visually examine the fabricated surface. The SEM scans the surface of a sample by using an electron beam, detects the secondary electrons emitted from the sample or the electrons reflected from the sample, and uses them to form an image of the scanned region.

The SEM is constructed to create a precise image that is as close to the shape of the sample's surface as possible in order to observe/measure the surface of the sample. The distance between two arbitrary points on the sample's surface can be computed from this created image.

This computation is generally called "critical dimension determination". The SEM having such computing function is referred to as the critical dimension SEM (CD-SEM). It is known that the electron beam irradiated in the semiconductor-measuring SEM is moderately accelerated, considering the damage to the sample, with energy of some hundreds of electron volts to reach the sample's surface that is to be observed.

Recently, the micro fabrication on the semiconductor surface has been progressed to further miniaturization in which a photoresist is used as a photosensitive material for photolithography (hereinafter, called ArF resist) that reacts to argon fluoride (ArF) excimer laser.

Since the ArF laser light has a short wavelength of 160 nm, it is said that the ArF resist is suited for the exposure of finer circuit patterns. However, from the recent examination, this resist is found very fragile to the irradiation of electron beam because, when the formed pattern is observed or measured by the SEM, the base material of acrylic acid resin induces condensation reaction due to the irradiation scanning of the focused electron beam to reduce the volume (hereinafter, called "shrink"), with the result that the shape of the circuit pattern changes.

On the other hand, the charged particle beam apparatus such as CD-SEM has the drawback that the image is blurred if the beam is not precisely focused on the sample's surface. In addition, if the image does not have sufficient brightness and contrast, it cannot be accurately measured. A document of, for example, JP-A-2001-68048 discloses that the image obtained when an electron beam scans an object being measured is used to make focus evaluation, and that the beam is adjusted on the basis of this evaluation.

SUMMARY OF THE INVENTION

However, even the electron beam used to obtain the above evaluation might damage the sample when it is irradiated. The electron beam irradiation particularly to the ArF resist should be avoided at all times before measurement, but the measurement precision cannot be increased without the above adjustment of each parameter. Thus, the damage to sample and the increase of measurement precision have a relation of tradeoff.

Accordingly, it is an objective of the invention to provide a charged particle beam apparatus capable of both reducing the damage to the object being measured and increasing the measurement precision.

To achieve the above objective, according to the invention, there is provided a method and apparatus adapted to detect charged particles released from a sample when a charged particle beam is irradiated on the sample to scan, create an image of a region over which said sample is scanned on the basis of the detected charged particles, and control the focus of the charged particle beam, the brightness of the image and/or the contrast of the image on the basis of the created image, characterized in that the focused state of the charged particle beam and the brightness of the image and/or the contrast of the image are controlled on the basis of a first image created when the charged particle beam is irradiated on the sample to scan a first pattern of the sample, and that the conditions under which the control for the focused state of the beam and the brightness and/or contrast is performed as above are stored and used so that the charged particle beam can be irradiated to properly scan a second pattern different from the first pattern.

According to the above construction, it is possible to reduce the amount of electron beam irradiated on the second pattern. Other constructions and effects of the invention will be apparent from the following description of the embodiments of the invention.

According to the invention, it is possible to provide a charged particle beam apparatus capable of both reducing the damage to an object to be measured and increasing the accuracy of measurement.

Other objects, features and advantages of the invention will become apparent from the following description of the embodiments of the invention taken in conjunction with the accompanying drawings.

DESCRIPTION OF THE EMBODIMENTS

Figure 1:
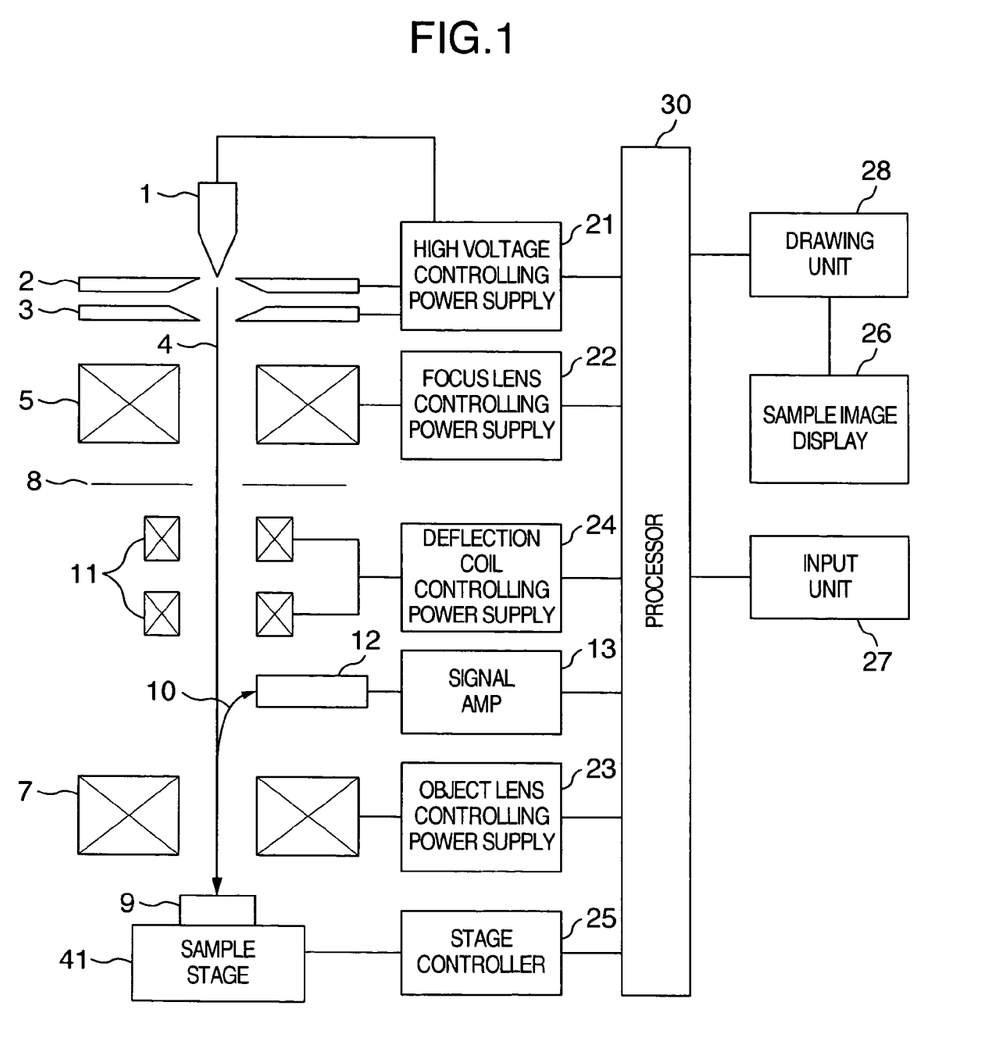
FIG. 1 is a schematic block diagram of the construction of an SEM.

FIG. 1 is a block diagram schematically showing an SEM of an embodiment according to the invention. Referring to FIG. 1, there are shown a cathode 1 and a first anode 2, between which a voltage is applied by a high-voltage controlling power supply 21 that is controlled by a processing device 30 (processor) to draw out a certain emission current from the cathode 1. Since an accelerating voltage is applied between the cathode 1 and a second anode 3 by the high-voltage controlling power supply 21 controlled by the processor 30, an electron beam 4 emitted from the cathode 1 is accelerated to advance to the following lens system. The electron beam 4 is converged by a focus lens 5 that is controlled by a focus lens controlling power supply 22. An aperture plate 8 removes unnecessary part of the electron beams 4.

Then, an object lens 7 controlled by an object lens controlling power supply 23 focuses the beam 4 on a very small spot of a sample 9. A deflector 11 is used to cause the beam spot to scan the sample 9 in a two-dimensional manner. The scanning signal to the deflector 11 is controlled depending on the observing magnification by a defection coil controlling power supply 24. The sample 9 is fastened on a sample stage 41 that is movable on a plane. The sample stage 41 is controlled to move by a stage controller 25.

A secondary electron detector 12 detects the secondary electrons, 10 generated from the sample 9 when the electron beam impinges on the sample. A drawing unit 28 converts the detected secondary signal to a visible signal, and controls it to be arranged on another plane so that a sample image display 26 can display the image corresponding to the surface shape of the sample as a sample image.

An input unit 27 acts as an interface between the operator and the processor 30. The operator handles this input unit 27 to control each of the above units or devices and to specify measurement points or issue commands for measurement of size. The processor 30 has a memory provided, though not shown, to store the measured values and the conditions under which each unit or device is controlled.

The signal detected by the secondary electron detector 12 is amplified by a signal amplifier 13, and accumulated in a picture memory provided within the drawing unit 28. While the secondary electron detector 12 is provided in this embodiment, it can be replaced by or used together with a reflected electron detector for detecting the reflected electrons or by a detector for detecting light, electromagnetic waves, X rays or ions.

The address signal corresponding to the locations of information in the picture memory is generated within the processor 30 or within a computer separately provided, converted to an analog signal, and then supplied to the deflector 11. If the picture memory is formed of, for example, 512×512 pixels, the X-direction address signal is a digital signal of a repeated range from 0 to 512, and the Y-direction address signal is also a digital signal of a repeated range from 0 to 512 that increments plus 1 each time the X-direction address signal has arrived at 512 from 0. This digital signal is converted to an analog signal.

Since the address to the picture memory is associated with the address for the deflecting signal by which the electron beam is deflected to scan, the picture memory stores a two-dimensional image representing the region within which the electron beam is deflected by the scanning coil. The signal stored within the picture memory can be sequentially read in a time-series manner by a read address generator that is synchronized with a read clock. The signal read out in association with the address is converted to an analog signal and supplied as a brightness modulation signal to the sample image display 28.

The apparatus of this embodiment according to the invention also has a function to form a line profile on the basis of the detected secondary electrons or reflected electrons. The line profile is formed on the basis of the amount of electrons detected or the brightness information of the sample image when the primary electron beam is deflected to scan in one-dimensional or two-dimensional way. The obtained line profile is used for the measurement of size of, for example, a pattern formed on a semiconductor wafer.

The measured size of pattern is displayed on the sample image display 26. On the display 26, two vertical or horizontal cursor lines are displayed together with the image, and these two cursors are brought to two edges of the pattern by handling the input unit 27 so that the size of the pattern can be computed by the processor 30 in accordance with the magnification of the sample image and the distance information between the two cursors.

The apparatus of this embodiment further has a function to align the charged particle beam spot and the scan position by using a unique pattern (matching pattern) at around the measurement location when the measurement location is specified on the semiconductor wafer. The memory stores this unique pattern image and the distance between this unique pattern and the image pattern being measured (or the amount of beam deflection and/or the amount of stage movement).

By matching this matching pattern to the actually acquired SEM image, it is possible to precisely grasp the field of view scanned by the electron beam and correctly position the beam scan range on the pattern being measured.

While the processor (controlling processor) is integrally or substantially integrally provided within the SEM as described above with reference to FIG. 1, it is of course not limited to that, but may be provided separately to make the following process. This case needs transmission media through which the signal detected by the secondary electron detector 12 is fed to the processor and through which the signal from the processor is supplied to the lens and deflector of the SEM, and input/output terminals for the signals to be transmitted through the transmission media.

In addition, a program for the process that will be described below may be registered in a recording medium, and executed by the processor that has the picture memory and supplies necessary signals to the SEM.

In addition, the apparatus of this embodiment has a function to previously store conditions (measurement locations or optical conditions for SEM) for the observation of, for example, a plurality of locations on a semiconductor wafer as a recipe, and to measure and observe according to the content of this recipe.

Also, a program for the process that will be described later may be registered in a recording medium, and executed by the processor that has a picture memory and supplies necessary signals to the SEM. In other words, the embodiments according to the invention which will be describe below are associated with the programs that can be employed in the charged particle beam apparatus such as SEM having the processor.

Embodiment 1

Figure 2:
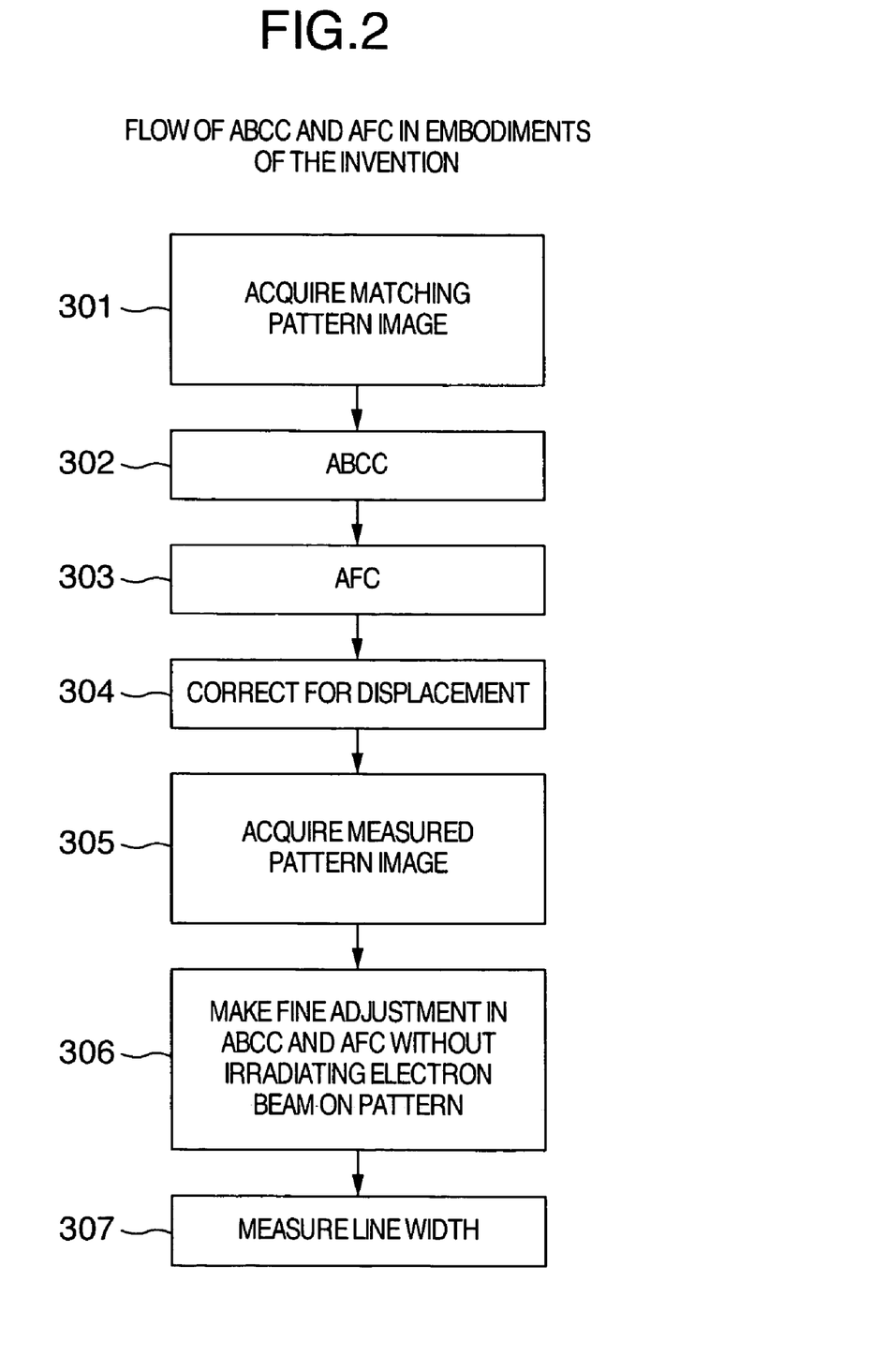
FIG. 2 is a flowchart of ABCC and AFC in the embodiments according to the invention.

FIG. 2 is a flowchart of the processes in which the measurement of line widths is performed. Referring to FIG. 2, a pattern to be desired to measure its line width is searched for and brought to the center of the field of view by moving the field of view to the matching pattern (first pattern) (S301). The matching pattern is a unique pattern that has a unique shape not existing around the neighborhood, and the coordinates of which are previously known on the wafer.

The stage on which the wafer is placed is moved to bring the matching pattern to the center of the field of view. Since the matching pattern is not always brought to the center of the field of view because the stage has positioning error, the particular shape of pattern is searched for to correct for the positioning error. At this time, if the matching pattern is not clear, it is sometimes failed to detect. For this purpose, ABCC is executed (S302). The ABCC is the abbreviation of the automatic brightness and contrast control. The process for ABCC is to adjust the amplification factor of the image signal detector system in order for a sufficiently bright image to be obtained. In addition, sine the image is required to have satisfactory contrast, the amplification factor of the image signal detector system is further adjusted so that the maximum and minimum values of the image signal can be fitted within the gradation width of brightness of image pixels.

After the ABCC is performed so that the image pattern including the matching pattern can be made clear, AFC is carried out (S303). AFC is the abbreviation of the automatic focus control. In the process for AFC, an image is produced by irradiating the electron beam on the pattern, and processed so that the sharpness of patterns can be quantified. The focus control parameter for the electronic optical system is gradually changed until this quantitative value (evaluation) can be optimized, and as a result a clearly focused, sharp image can be obtained. The parameters obtained in the ABCC (S302) and AFC (S303) are stored in the memory.

Since the image pattern is now clear and sharp, the matching pattern can be more accurately searched for within the image. Then, the correction for the displacement is made (S304), and the matching pattern can be brought to the center of the field of view by adjusting. When this adjustment is made, the stage is not moved but the electron beam is moved in parallel to move the matching pattern in the field of view.

Since the positioning error of the stage can be corrected for by the above steps, the field of view is this time moved to the pattern being measured (second pattern) (S305). Since information of the relative position of the measured pattern to the matching pattern is previously known, the beam is shifted by this amount so that the measured pattern can be positioned around the center of the image.

Here, ABCC and AFC are not made for the measured pattern, but the ABCC and AFC control parameters obtained from the matching pattern are used to acquire the image data of the measured pattern. The parameters for ABCC may be found from the image data that is previously acquired from the matching pattern.

In the prior art, ABCC and AFC are substantially made each time an image is acquired. ABCC and AFC are made on the basis of the image signal detected when the electron beam is actually irradiated on the region of filed of view. However, when the pattern has a property such as ArF resist that shrinks due to the irradiation of electron beam, the pattern might shrink while the ABCC and AFC are being performed to acquire the image. This means that error occurs in the line width measurement at the instant when ABCC and AFC are made.

According to this embodiment, control parameters (conditions for adjustment) for ABCC and AFC are estimated by using the matching pattern for which the damage to shrink can be allowed unlike the measured pattern for which ABCC and AFC are restricted not to make (S306).

The matching pattern is located near the measured pattern, and fully scanned by the electron beam to produce the image before the beam reaches the measured pattern. Therefore, by the above process it is possible to precisely find the control parameters without reducing the throughput.

According to this embodiment, the precision of the measured values can be increased under the restriction of ABCC and AFC not to make. On a sample such as a semiconductor wafer that has a number of matching patterns and measured patterns, the matching patterns can be selectively utilized to acquire the evaluations of ABCC and AFC, and thus the damage to the measured patterns can be reduced.

Figure 3:
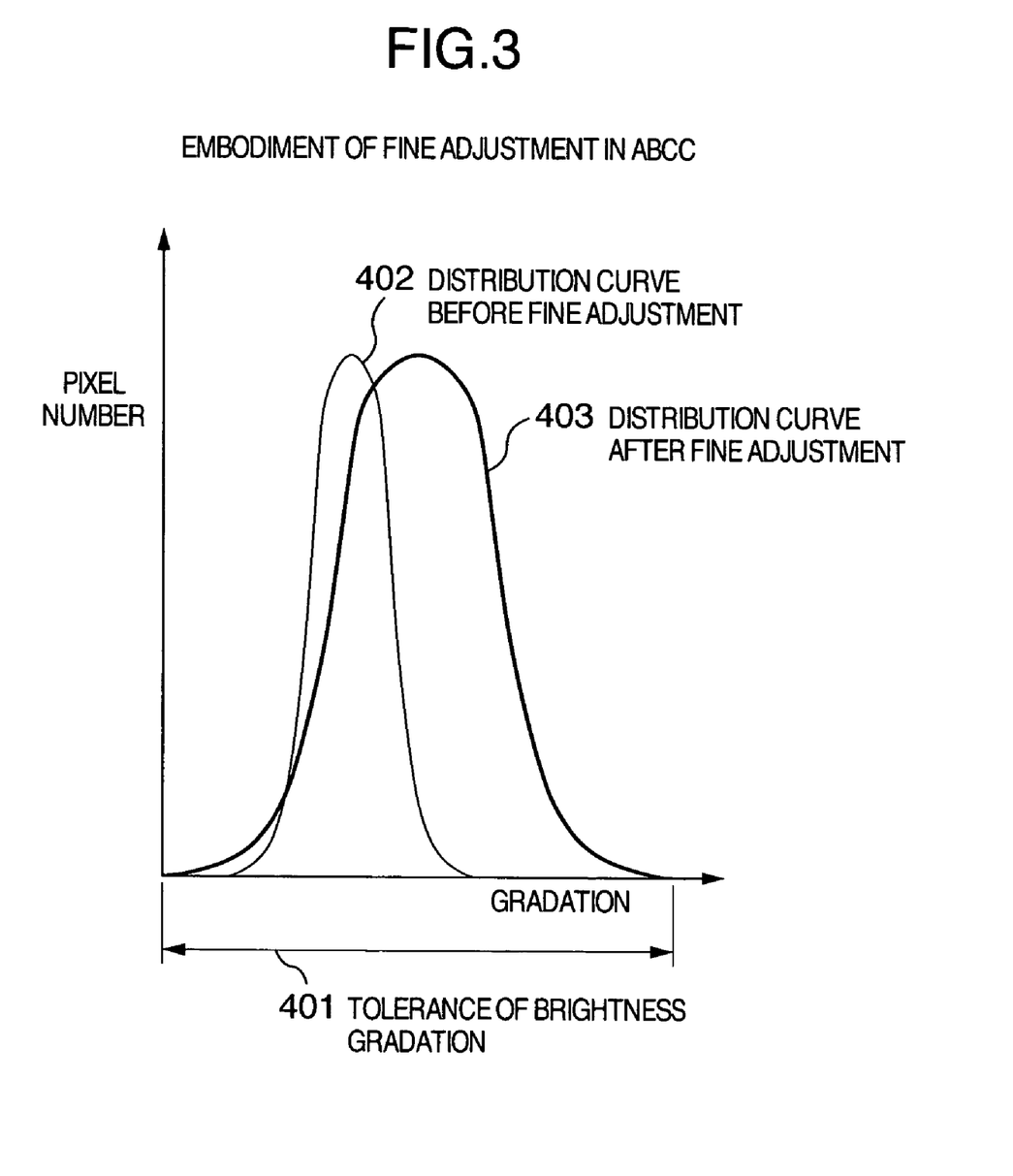
FIG. 3 is a diagram to which reference is made in explaining an example of the fine adjustment of ABCC.

In order to measure, it is necessary to obtain as clear images as possible. Thus, processing of image (correction for brightness and contrast) is performed. A method for the process will be described as, for example, given below. A histogram is produced of the brightness gradations of the pixels that constitute an image. FIG. 3 shows an example of the histogram. The abscissa indicates the gradation, and the ordinate the number of pixels having the corresponding gradation. The upper and lower limits of the brightness gradation define a tolerance 401 of brightness gradation as illustrated.

The distribution of gradations of pixels of the measured pattern that is obtained by using the control parameters found in the processes of ABCC (S302) and AFC (S303) is indicated as a distribution curve 402 before fine adjustment. Since the above control parameters are obtained for the matching pattern, the control parameters for the measured pattern have a delicate difference to those for the matching pattern. In this example, the width of the distribution curve 402 before fine adjustment is narrower than that of the tolerance 401 of the brightness gradation. Thus, since the fine adjustment which will be made later can be satisfactorily performed under this condition, the parameters for ABCC (S302) are not directly used, but slightly deviated so that the distribution curve 402 before fine adjustment can always be fitted within the tolerance 401 of the brightness gradation.

Since the center of the distribution curve 402 before fine adjustment is located near the darker side away from the center of the tolerance 401 of the brightness gradation, the image of the measured pattern is somewhat darker, and thus the measured value cannot be correctly found unless the definition is adjusted. In addition, since the width of the distribution curve 402 before fine adjustment is spread only about half that of the tolerance 401 of the brightness gradation, the contrast of the image is insufficient, and the precision of measured value is still poor. Thus, the gradations of pixel are finely adjusted as, for example, given below.

Of the pixels arranged in x rows and y columns, the pixels before fine adjustment are represented by p(x, y), and the pixels after fine adjustment by p'(x, y). At this time, fine adjustment is performed so that the following equation can be satisfied.

$$p'(x, y) = A \times p(x, y) + B \quad (1)$$

where A and B are parameters for adjustment.

The gradations of p'(x, y) provide a distribution curve 403 after fine adjustment. Since the center of the distribution curve 403 of p'(x, y) after fine adjustment comes to substantially the center of the tolerance 401 of the brightness gradation, the image of the measured pattern is improved in its sharpness. In addition, since the width of the distribution curve 403 after fine adjustment is fully spread to cover the tolerance 401 of the brightness gradation, the contrast of the image is improved. Therefore, the precision of the measured value is increased since the picture quality of the measured pattern is improved. Moreover, since the above method does not actually irradiate the electron beam, shrinking does not occur.

The processing of image (S307) is followed by AFC in which the number of times the beam is deflected to scan is kept constant. Although the control loop is repeated until the AFC is settled, the number of times the loop is repeated is not constant but fluctuated. Thus, the electron beam of different amounts is irradiated on the measured pattern in the process for AFC each time the measurement is made for line width, thus changing the amounts of electrostatic charges and contamination caused by this irradiation so that the measured value fluctuates.

Here, the beam scanning is surely made L times to solve this problem. Even if the number of time the beam scanning is made for optimizing the AFC is lower than L, the beam scanning is continued until the number of times of beam scanning reaches L. Thus, the amounts of electron beam irradiation scattered each time the line width is measured become constant at all times, and the amount of shrinking is settled constant. Therefore, the precision of measurement can be prevented from being degraded by the fluctuation of the amounts of shrinking. Thereafter, the line widths of the measured pattern on the image are measured with less amounts of shrinking and with high precision. The focus control can be made by controlling the object lens to focus the beam on the sample or by controlling the voltage applied to the sample so as to adjust the energy with which the charged particle beam can reach the sample.

Figure 4:
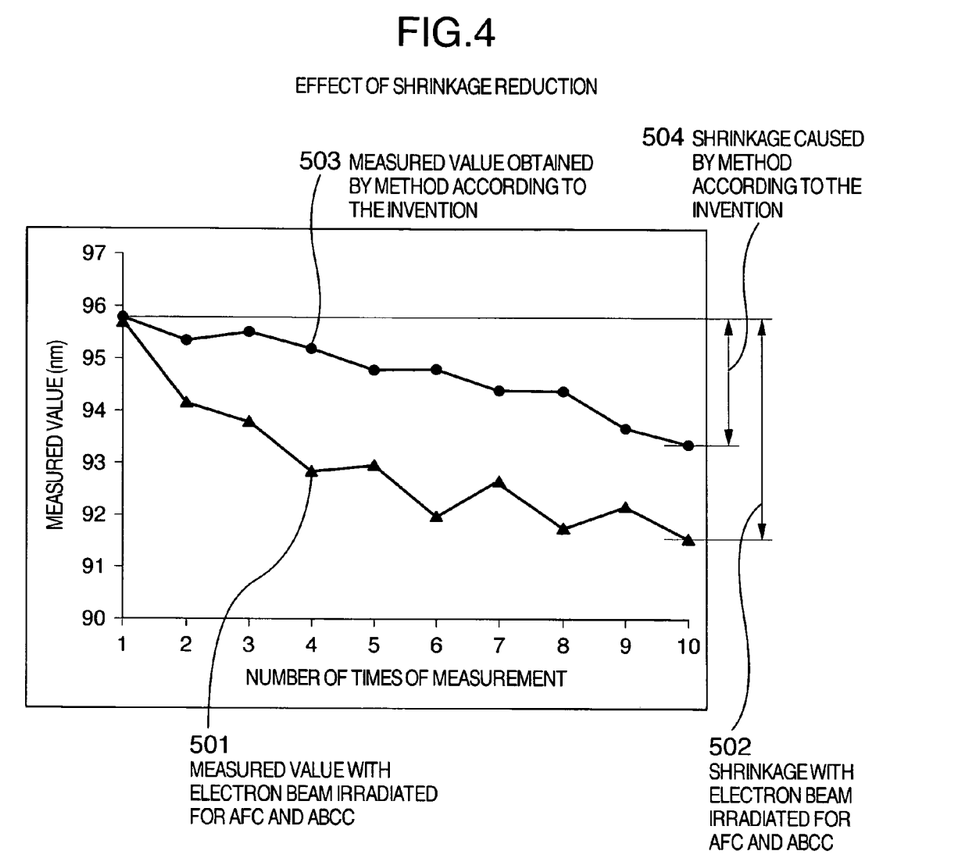
FIG. 4 is a graph showing the effect of reducing the amount of shrink.

FIG. 4 is a graph showing the effect of the construction mentioned above. A measured value 501 indicates the case where ABCC is made when the beam is actually irradiated. The measured value 501 is decreased to increase the amount of shrink each time the measurement is made. The shrinkage after 10 times of measurement becomes a considerable amount as indicated by 502. The measured value, 503, obtained by using the method according to the invention is also decreased, but causes less amounts of shrinkage as indicated by 504.

Since the electron beam for ABCC is not irradiated on the measured pattern in the method according to the invention, the amount of shrinkage can be reduced to about half that of the case in which the beam for ABCC is irradiated on the measured pattern.

Moreover, since AFC is performed with the beam irradiated to scan constant times, electrostatic charges and contamination can be prevented from being caused by the fluctuation of the amounts of the irradiated beam. As a result, the measured value becomes constant because there is no electrostatic charges and contamination. Therefore, the data of shrinkage 504 clearly shows that the dispersion of measured value 503 is smaller than that of measured value 501.

An example has so far been shown in which AFC and ABCC are made for the matching patterns so that the control parameters for the processes can be used when the image of the measured pattern is acquired. However, the patterns from which the control parameters are obtained are not necessary to be the matching patterns, but may be any pattern near the measured patterns.

Embodiment 2

Figure 5:
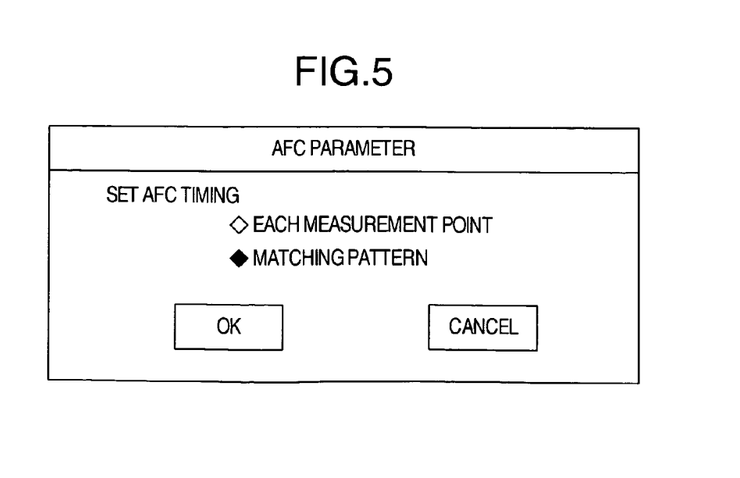
FIG. 5 shows a GUI dialog box that asks the user to select an AFC condition.

FIG. 5 shows a GUI (Graphical User Interface) dialog box through which the user selects any one of the conditions under which AFC is performed. The apparatus of this embodiment according to the invention has a function to previously store the conditions (positions at which measurement is made, and optical conditions of SEM) as a recipe to be used when a plurality of points on the sample are observed and to measure and observe according to the content of the recipe. The processor 30 in the apparatus according to the embodiment controls the SEM according to the conditions of the recipe. The GUI dialog box shown in FIG. 5 is used to set the AFC timing of a plurality of control conditions. The GUI dialog box is handled by using, for example, a pointing device not shown.

On the GUI dialog box shown in FIG. 5, the operator can select each measurement point for AFC or matching pattern for AFC. By providing the selection means, it is possible to arbitrarily select that the matching patterns are used for AFC in order for the damage to the measured patterns to be reduced or that each measured pattern is used for AFC in order for the measurement precision to be increased.

Since there are some kinds of samples that are not damaged so much by the irradiation of electron beam, the above option is provided so that the operator can arbitrarily select either the reduction of damage for AFC or the high precision for AFC to measure the line widths with high accuracy on the basis of sample conditions or operator's experience.

While the GUI dialog box shown in FIG. 5 is provided so that the timing for AFC can be directly set, it may be changed so that the kind of sample, for instance, can be entered. If the GUI dialog box is formed to make it possible to arbitrarily select any one of sample materials that might be damaged or not by the irradiation of electron beam, the same effect as in FIG. 5 can be achieved.

Embodiment 3

This embodiment is the same as the embodiment 1 as far as it includes the processes to make AFC and/or ABCC for the first pattern (for example, matching pattern), acquire the second pattern (measured pattern) by using the obtained parameters and adjust the contrast and brightness by image processing. However, the process of focusing that follows the above processes is different from that in the embodiment 1. In this embodiment, a Z-sensor for height is provided in the SEM and used to previously detect the height difference between the matching pattern and the measured pattern. The electron beam is focused on the measured pattern by using the parameters of matching pattern for AFC and the height difference.

With this construction, AFC can be made without the irradiation of electron beam on the measured pattern, and the amount of electron beam irradiated on the measured pattern can be reduced. The focus control can be performed by adjusting the object lens to focus the beam on the sample or by adjusting the voltage (retarding voltage) applied to the sample in order to adjust the energy with which the charged particle beam can reach the sample.

Embodiment 4

In this embodiment, when the height difference between the matching pattern and the measured pattern is previously known from design values or others, the amount of focus control for supplementing that height difference is previously stored, the focus control is performed for the matching pattern, and then the focus control is made for the measured pattern on the basis of the control parameters used in the former focus control and of the amount of supplemental focus control. According to the construction of this embodiment, substantially the same focus control for the measured pattern can be performed without creating an image for the focus control.

While the SEM has been described as one of the charged particle beam apparatus as the above embodiments according to the invention are given above, the present invention can be applied to other charged particle beam apparatus such as ion beam apparatus for creating images by irradiating an ion beam on a sample.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A method of adjusting in a charged particle beam apparatus constructed to irradiate a charged particle beam on a sample to scan said sample, detect charged particles obtained by said irradiation, create an image of a region over which said sample is scanned on the basis of said detected charged particles, and control the focus of said charged particle beam and the brightness of said image and/or contrast of said image on the basis of said created image, said method comprising the steps of:
   creating a matching pattern when said charged particle beam is irradiated on said sample to scan a matching pattern of said sample;
   controlling the focus of said charged particle beam and the brightness of said image and/or contrast of said image on the basis of said image of said matching pattern on the basis of an irradiation of said charged particle beam on said sample to scan said sample;
   performing an alignment to scan of said charged particle beam, on the basis of said image of said matching pattern which has the controlled focus of said charged particle beam and the controlled brightness of said image and/or the controlled contrast of said image; and
   irradiating said charged particle beam on said sample to scan a measuring pattern, wherein a position of said measuring pattern is identified by said matching pattern by using control conditions of said charged particle beam which has the controlled focus of said charged particle beam and the controlled brightness of said image and/or the controlled contrast of said image.

2. A method according to claim 1, wherein said focus control is performed by an object lens to focus said charged particle beam on said sample or by controlling the voltage applied to said sample in order to adjust the energy with which said charged particle beam reaches said sample.

3. A method according to claim 1, wherein said brightness of said image and/or said contrast of said image can be controlled by adjusting the gradations of said image.

4. A method according to claim 3, wherein gradations which are set to said image of said matching pattern and controlled by predetermined adjusting parameters are applied to form an image of said measuring pattern.

5. A method according to claim 1, wherein said irradiation of said beam to scan said measuring pattern is performed by using the conditions under which said beam is focused on said matching pattern and focus control parameters determined on the basis of the height difference between said matching pattern and said measuring pattern.

6. A charged particle beam apparatus comprising:
   a charged particle beam source;
   a scan deflector for deflecting a charged particle beam emitted from said charged particle beam source to scan on a sample;
   a detector for detecting charged particles obtained by an irradiation of said charged particle beam on said sample; and
   a controller for creating an image on the basis of the output from said detector, wherein
   said controller creates a first image when said charged particle beam is irradiated on said sample to scan a matching pattern of said sample, controls the focus of said charged particle beam and the brightness of said image and/or contrast of said image on the basis of said image of said matching pattern, performs an alignment to scan of said charged particle beam, on the basis of said image of said matching pattern which has the controlled focus of said charged particle beam and the controlled brightness of said image and/or the controlled contrast of said image, and irradiates said charged particle beam on said sample to scan a measuring pattern, wherein a position of said measuring pattern is identified by said matching pattern by using control conditions of said charged particle beam which has the controlled focus of said charged particle beam and the controlled brightness of said image and/or the controlled contrast of said image.

7. A charged particle beam apparatus according to claim 6, wherein said controller performs the focus control by controlling the voltage applied to said sample in order to control an object lens to focus said charged particle beam on said sample or the energy with which said charged particle beam reaches said sample.

8. A charged particle beam apparatus according to claim 6, wherein said controller controls the brightness of said image and/or contrast of said image by adjusting gradations of said image.

9. A charged particle beam apparatus according to claim 8, wherein said controller applies gradations which are set to said image of said matching pattern and controlled by predetermined adjusting parameters to form an image of said measuring pattern.

* * * * *